United States Patent
Atkinson et al.

(10) Patent No.: US 8,422,750 B2
(45) Date of Patent: Apr. 16, 2013

(54) RETINAL SCANNING

(75) Inventors: Alastair Atkinson, Edinburgh (GB); Christophe Mazo, Le Pecq (FR)

(73) Assignee: Optos, PLC, Fife (GB)

( * ) Notice: Subject to any disclaimer, the term of this patent is extended or adjusted under 35 U.S.C. 154(b) by 725 days.

(21) Appl. No.: 12/312,421

(22) PCT Filed: Nov. 1, 2007

(86) PCT No.: PCT/GB2007/004185
§ 371 (c)(1), (2), (4) Date: Feb. 22, 2010

(87) PCT Pub. No.: WO2008/056110
PCT Pub. Date: May 15, 2008

(65) Prior Publication Data
US 2010/0150415 A1     Jun. 17, 2010

(30) Foreign Application Priority Data

Nov. 9, 2006   (GB) .................................. 0622325.9

(51) Int. Cl.
*G06K 9/00* (2006.01)
(52) U.S. Cl.
USPC ........... 382/128; 382/117; 359/443; 359/291; 348/78; 345/8; 250/559.36
(58) Field of Classification Search .................. 382/117; 359/443, 291, 221, 211; 348/78; 345/8; 250/559.36
See application file for complete search history.

(56) References Cited

U.S. PATENT DOCUMENTS

| | | | |
|---|---|---|---|
| 5,815,242 A | | 9/1998 | Anderson et al. |
| 6,008,781 A | * | 12/1999 | Furness et al. .................... 345/8 |
| 6,639,570 B2 | * | 10/2003 | Furness et al. .................... 345/8 |
| 6,810,140 B2 | * | 10/2004 | Yang et al. ..................... 382/154 |
| 7,001,019 B2 | * | 2/2006 | Takagi et al. ................. 351/211 |
| 7,404,640 B2 | * | 7/2008 | Ferguson et al. ............. 351/221 |
| 2002/0034006 A1 | * | 3/2002 | Kostrzewski et al. ........ 359/443 |
| 2002/0176619 A1 | * | 11/2002 | Love ............................. 382/154 |
| 2007/0018124 A1 | * | 1/2007 | Nishi ....................... 250/559.36 |
| 2007/0110285 A1 | * | 5/2007 | Hanna et al. ................. 382/117 |
| 2009/0122385 A1 | * | 5/2009 | Hilton ........................... 359/291 |
| 2009/0268020 A1 | * | 10/2009 | Buckland et al. .............. 348/78 |

OTHER PUBLICATIONS

Google search results, Jun. 14, 2012.*
Google patents search result, Jan. 3, 2012.*

(Continued)

*Primary Examiner* — Dilek B Cobanoglu
(74) *Attorney, Agent, or Firm* — Drinker, Biddle & Reath, LLP

(57) ABSTRACT

A method and apparatus of producing a three-dimensional image of at least a part of the retina of an eye is provided. The method including obtaining a two-dimensional wide-field image of said part of said retina, determining a three-dimensional shape for said part of said retina and using the three-dimensional shape for said part of said retina to modify said two-dimensional image to produce a three-dimensional image of said part of said retina. The apparatus including an imaging system adapted to provide a two-dimensional wide-field image of said part of said retina, a three-dimensional shape determination module adapted to determine a three-dimensional shape for said part of said retina, and a two-dimensional image modification module adapted to modify said two-dimensional wide-field image of said part of said retina using said three-dimensional shape to produce a three-dimensional image of said part of said retina.

14 Claims, 3 Drawing Sheets

OTHER PUBLICATIONS

P.-Y Bondiau et al., "Eye Reconstruction and CT-Retinography Fusion for Proton Treatment Planning of Ocular Diseases", CVRMED-MRCAS '97, First Joint Conference, Computer Vision, Virtual Reality and Robotics in Medicine and Medical Robotics and Computer-Assisted Surgery Proceedings Springer-Verlag Berlin, Germany, 1997, pp. 705-714.

Tae Eun Choe et al., "Evaluation of 3-D Shape Reconstruction of Retinal Fundus," Medical Image Computing and Computer-Assisted Intervention-MICCAI 2006 Lecture Notes in Computer Science; LNCS, Springer Berlin Heidelberg, BE, Sep. 26, 2008, pp. 134-141, vol. 4190.

* cited by examiner

RETINAL SCANNING

The present invention relates to a method of producing a three-dimensional image of at least a part of the retina of an eye and an apparatus for the same.

Fundus cameras and scanning ophthalmoscopes obtain two-dimensional images of the retina of the eye. These imaging systems project the curved spherical surface of the retina on a two-dimensional image.

Whilst the images obtained from these systems are of high quality, they are limited in that they only present an accurate image of the retina around the central axis of the eye. Imaged areas around the peripheral retina are skewed to such an extent that it is difficult to obtain a meaningful image.

It is important for disease diagnosis and monitoring to observe the true dimensions of retinal features. For example, an ophthalmologist may wish to assess the size of a cancer tumour and may want to monitor its growth. This is difficult to achieve with two-dimensional images of the retina.

It is an object of the present invention to provide a method of producing a three-dimensional image of the retina of an eye and an apparatus for carrying out the same which obviates or mitigates one or more of the disadvantages referred to above.

According to a first aspect of the present invention there is provided a method of producing a three-dimensional image of at least a part of the retina of an eye comprising the steps of:
  obtaining a two-dimensional wide-field image of said part of said retina;
  determining a three-dimensional shape for said part of said retina;
  using the three-dimensional shape for said part of said retina to modify said two-dimensional image to produce a three-dimensional image of said part of said retina.

The step of obtaining said two-dimensional wide-field image of said part of said retina may include receiving a previously-recorded image of said part of said retina.

The step of obtaining said two-dimensional wide-field image of said part of said retina may include scanning said part of said retina with collimated light.

Preferably, said two-dimensional wide-field image of said part of said retina is modified by mapping a portion of said image to said three-dimensional shape for said part of said retina to produce said three-dimensional image of said part of said retina.

Preferably, scanning said part of said retina with said collimated light includes:
  providing a source of said collimated light, a first scanning element, a second scanning element and a scan compensator;
  using said source of said collimated light, said first and second scanning elements and said scan compensator in combination to provide a two-dimensional collimated light scan from an apparent point source;
  providing a scan transfer device having two foci;
  providing said apparent point source at a first focus of said scan transfer device and accommodating said eye at said second focus of said scan transfer device; and
  using said scan transfer device to transfer said two-dimensional collimated light scan from said apparent point source to said eye to obtain a two-dimensional wide-field image of said part of said retina.

Preferably, the step of determining said three-dimensional shape for said part of said retina includes the steps of:
  assigning a shape to the whole of said retina;
  identifying the position of said part of said retina with respect to said whole of said retina; and
  using said assigned shape and said position of said part of said retina to determine said three-dimensional shape for said part of said retina.

Preferably, the step of assigning a shape to said whole of said retina includes selecting a general shape which approximates the shape of an eye.

Preferably, the step of assigning a shape to said whole of said retina includes measuring at least one parameter of said retina, using said at least one parameter to modify said general shape to obtain a specific shape of said whole of said retina of said eye, and assigning said specific shape to said whole of said retina.

Preferably, said general shape is an ellipsoid and said parameter may include the major axis or minor axis of said whole of said retina.

Preferably, the step of identifying said position of said part of said retina with respect to said whole of said retina includes:
  determining the path of said collimated light used to obtain said two-dimensional wide-field image of said part of said retina; and
  calculating the position of intersection of said path of said collimated light with said specific shape of said whole of said retina.

Preferably, the step of calculating the position of intersection of said path of said collimated light with said specific shape of said whole of said retina includes the further step of determining the position of said whole of said retina relative to an ideal position of said whole of said retina.

Preferably, the step of determining said path of said collimated light includes calculating said path of said collimated light from said source of collimated light to said retina.

Preferably, said calculation of said path of said collimated light includes determining distortion of said collimated light produced by said scan compensator.

Preferably, said calculation of said path of said collimated light includes determining distortion of said collimated light produced by said scan transfer device.

Preferably, said calculation of said path of said collimated light includes determining distortion of said collimated light produced by the cornea of said eye.

Preferably, said calculation of said path of said collimated light includes determining distortion of said collimated light produced by the lens of said eye.

Preferably, said two-dimensional wide-field image of said part of said retina comprises a plurality of pixels.

Preferably, said two-dimensional wide-field image of said part of said retina is modified by mapping said plurality of pixels to said three-dimensional shape for said part of said retina to produce said three-dimensional image of said part of said retina.

Preferably, said mapping of said plurality of pixels includes interpolating image data contained in one or more of said pixels.

According to a second aspect of the present invention there is provided an apparatus for producing a three-dimensional image of at least a part of the retina of an eye comprising:
  an imaging system adapted to provide a two-dimensional wide-field image of said part of said retina;
  a three-dimensional shape determination module adapted to determine a three-dimensional shape for said part of said retina; and
  a two-dimensional image modification module adapted to modify said two-dimensional wide-field image of said part of said retina using said three-dimensional shape to produce a three-dimensional image of said part of said retina.

Preferably, said imaging system comprises:
a source of collimated light;
a first scanning element;
a second scanning element; and
a scan compensator;
wherein said source of collimated light, said first and second scanning elements and said scan compensator combine to provide a two-dimensional collimated light scan from an apparent point source;
said apparatus further comprising a scan transfer device, wherein said scan transfer device has two foci and said apparent point source is provided at a first focus of said scan transfer device and an eye is accommodated at a second focus of said scan transfer device, and wherein said scan transfer device transfers said two-dimensional collimated light scan from said apparent point source into said eye to obtain a two-dimensional image of said part of said retina.

An embodiment of the present invention will now be described, by way of example only, with reference to the accompanying drawings, in which.

Figure 1:
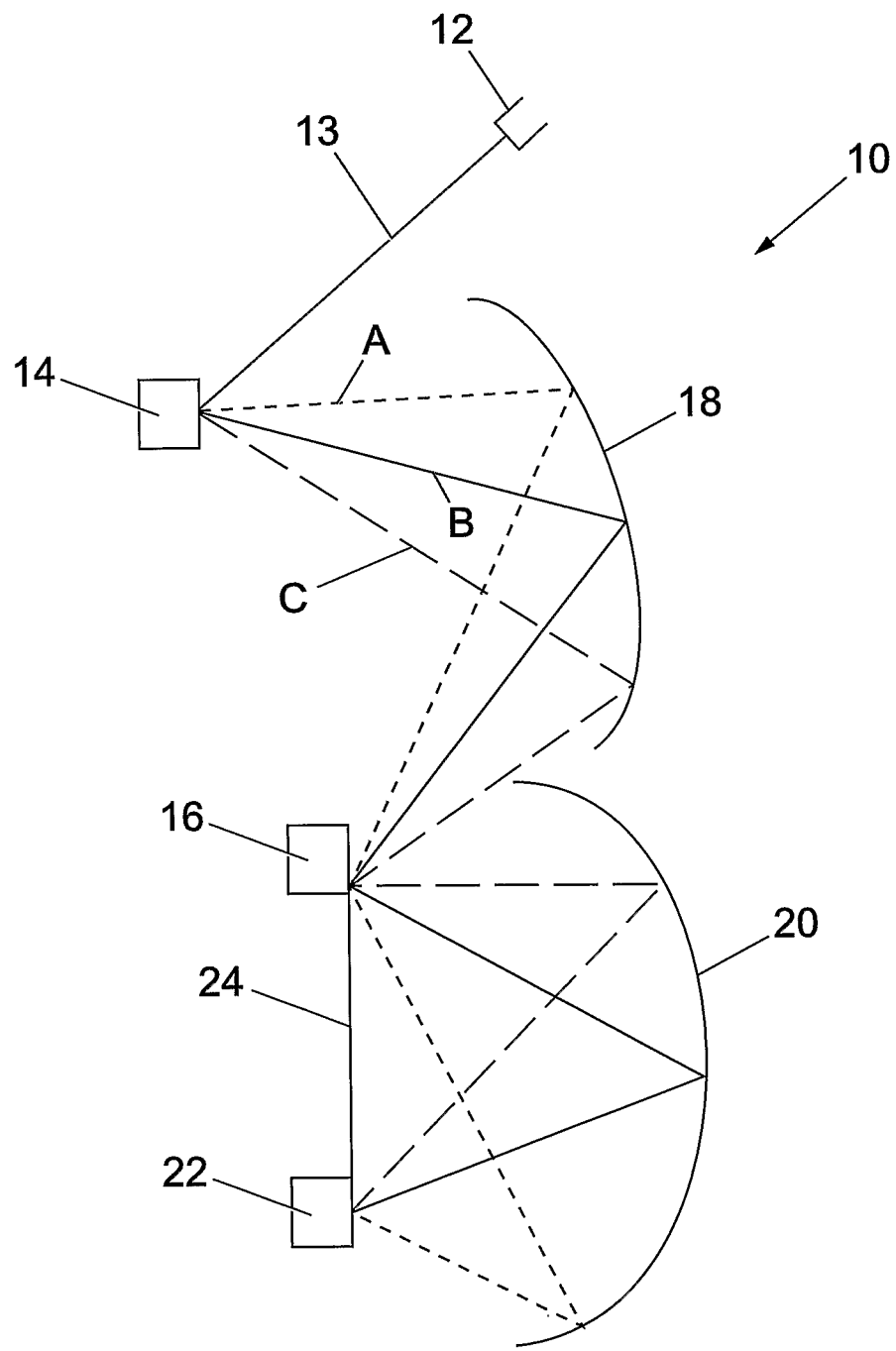
FIG. 1 is an optical schematic of an imaging system, comprising a scanning ophthalmoscope, and indicates an incident path from a source of collimated light of the system to a subject's eye.

With reference to FIG. 1, the imaging system comprises a scanning ophthalmoscope 10, which in turn, comprises a source of collimated light 12 producing collimated light 13, a first scanning element 14, a second scanning element 16, a scan compensator 18 and a scan transfer device 20.

The source of collimated light 12 is a laser, and the collimated light 13 produced by the source 12 is a laser beam. The first scanning element 14 is a high speed rotating polygon mirror and the second scanning element 16 is a slow speed oscillating plane mirror. The polygon mirror 14 and the oscillating plane mirror 16 are arranged to create a two-dimensional scan, in the form of a raster scan pattern, of the laser beam 13.

The polygon mirror 14 has a plurality of facets, and provides a plurality of first one-dimensional scans. On rotation of the polygon mirror 14, each facet of the polygon mirror 14 generates a vertical one-dimensional scan of the laser beam 13, which forms a vertical scan component of the raster scan pattern. FIG. 1 illustrates the path of the laser beam 13 in a vertical one-dimensional scan produced by one facet of the polygon mirror 14, as this facet is rotated. Path A is an example of the laser beam 13 reflected from the polygon mirror 14 at the start of the rotation; path B is an example of the laser beam 13 reflected from the polygon mirror 14 at an intermediate point of the rotation; and path C is an example of the laser beam 13 reflected from the polygon mirror 14 at the end of the rotation.

The oscillating plane mirror 16 provides a second one-dimensional scan. On oscillation of the plane mirror 16, the mirror generates a horizontal one-dimensional scan of the laser beam 13, which forms a horizontal scan component of the raster scan pattern. The polygon mirror 14 and the oscillating plane mirror 16 thus together create a two-dimensional scan in the form of the raster scan pattern.

The scan compensator 18 is an ellipsoidal mirror, having two foci, and is referred to as a slit mirror. It should be appreciated, however, that the scan compensator 18 may have an alternative form having two foci. The polygon mirror 14 is positioned at a first focus of the slit mirror 18 and the oscillating plane mirror 16 is positioned at the second focus of the slit mirror 18.

The scan transfer device 20 is an aspherical mirror in the form of an ellipsoidal mirror, having two foci, and is referred to as a main mirror. It will again be appreciated, however, that the scan transfer device 20 may have an alternative form having two foci. The oscillating plane mirror 16 is also positioned at a first focus of the main mirror 20. A subject's eye 22 is positioned at a second focus of the main mirror 20.

The laser beam 13 is thus conveyed to the subject's eye 22, via the polygon mirror 14, the slit mirror 18, the oscillating plane mirror 16 and the main mirror 20. The polygon mirror 14, the slit mirror 18, and the oscillating plane mirror 16, combine to provide the two-dimensional scan of the laser beam 13, in the form of the raster scan pattern as described above, from an apparent point source positioned at the first foci of the scan transfer device 20. The scan of the laser beam 13 is coupled from the oscillating plane mirror 16 to the subject's eye 22, by the main mirror 20, and a part of the retina of the subject's eye is thereby scanned by the laser beam 13.

The scan of the laser beam 13 is reflected from the part of the retina of the subject's eye 22, and is conveyed back through the scanning ophthalmoscope, and is used to produce an image of the part of the subject's retina. The scanning ophthalmoscope 10 therefore obtains a two-dimensional wide-field image of the part of the retina.

The scan compensator slit mirror 18 transfers the laser beam 13 from the polygon mirror 14 to the oscillating plane mirror 16. The scan compensator slit mirror 18 provides point to point transfer, without introducing any translational component, which would cause failure of the laser beam 13 to enter through the pupil of the subject's eye. Thus the laser beam 13 appears to come from an apparent point source.

Since the polygon mirror 14 is positioned at the first focus of the slit mirror 18, light from the polygon mirror 14 will always be reflected through the second focus of the slit mirror 18, regardless of the angle of deflection of light from the polygon mirror 14 onto the slit mirror 18. Similarly, since the oscillating plane mirror 16 is also positioned at the first focus of the main mirror 20, light from the oscillating plane mirror 16 will always be reflected through the second focus of the main mirror 20, regardless of the angle of deflection of light from the oscillating plane mirror 16. Since the subject's eye 22 is positioned at the second focus of the main mirror 20, the raster scan pattern of the laser beam 13 is transmitted without disruption through the pupil of the subject's eye 22.

The scan compensator slit mirror 18 also acts as a scan angle amplifier. Each facet of the polygon mirror 14 produces a vertical one-dimensional scan of the laser beam 13, comprising a "fan" of laser light rays. These rays travel to the slit mirror 18. The rays are then brought to focus at the oscillating plane mirror 16. According to the eccentricity of the slit mirror 18, there will be scan angle amplification. As a result of the above, the scanning ophthalmoscope 10 may be able to produce up to 150 degree scans, for example 120 degrees, 110 degrees, 90 degrees, 60 degrees, 40 degrees, of the part of the retina of the subject's eye 22, measured at the pupillary point of the eye. The scanning ophthalmoscope 10 is therefore able to obtain two-dimensional wide-field images of the retina, or a part of the retina.

The two-dimensional wide-field image of the part of the retina of the subject's eye 22 produced by the scanning ophthalmoscope 10 is affected by a number of distortions that occur both within the scanning ophthalmoscope 10 and the subject's eye.

These distortions may be corrected as follows:

(a) Scanning Ophthalmoscope Distortions

As described above, the laser beam 13 is conveyed to the subject's eye 22 via the polygon mirror 14, the slit mirror 18, the oscillating plane mirror 16 and the main mirror 20. The polygon mirror 14, the slit mirror 18 and the oscillating plane mirror 16 combine to provide a two-dimensional scan of the laser beam 13 in the form of a raster scan pattern from an apparent point source.

As illustrated in FIG. 1, the laser beam 13 is scanned across the slit mirror 18 and the main mirror 20 in the direction of their major axis (i.e. for each mirror, the line joining the foci of the mirror). Scanning in this direction across the slit mirror 18 and the main mirror 20, introduces a distortion into the vertical scan component of the raster scan pattern. The effect of this is that the image obtained from the scanning ophthalmoscope 10 is skewed in the vertical direction.

The distortion thus introduced into the image may be determined by creating a mathematical model of the scanning ophthalmoscope 10. The model may be used to determine the undistorted, path of the laser beam 13 as it propagates through the scanning ophthalmoscope 10, i.e. from the source of collimated light (laser 12) to the retina of the subject's eye 22. The difference between the measured, i.e. distorted, path of the laser beam 13 and the undistorted path of the laser beam provides the distortion introduced by the slit mirror 18 and the main mirror 20 to the vertical scan component of the raster scan pattern.

Once this distortion is determined, a correction may be applied to the retinal image to substantially remove the effects of this distortion on the retinal image. Since this distortion is specific to the scanning ophthalmoscope 10, the same correction may be applied to every image obtained therefrom.

Verification of the correction applied to the two-dimensional wide-field retinal image may be confirmed by imaging a reference image (e.g. a grid). The image of the grid obtained by the scanning ophthalmoscope 10 without application of any correction will be distorted in the vertical direction. With the correction applied the imaged grid will appear substantially identical to the actual grid.

(b) Eye Distortions

Figure 2:
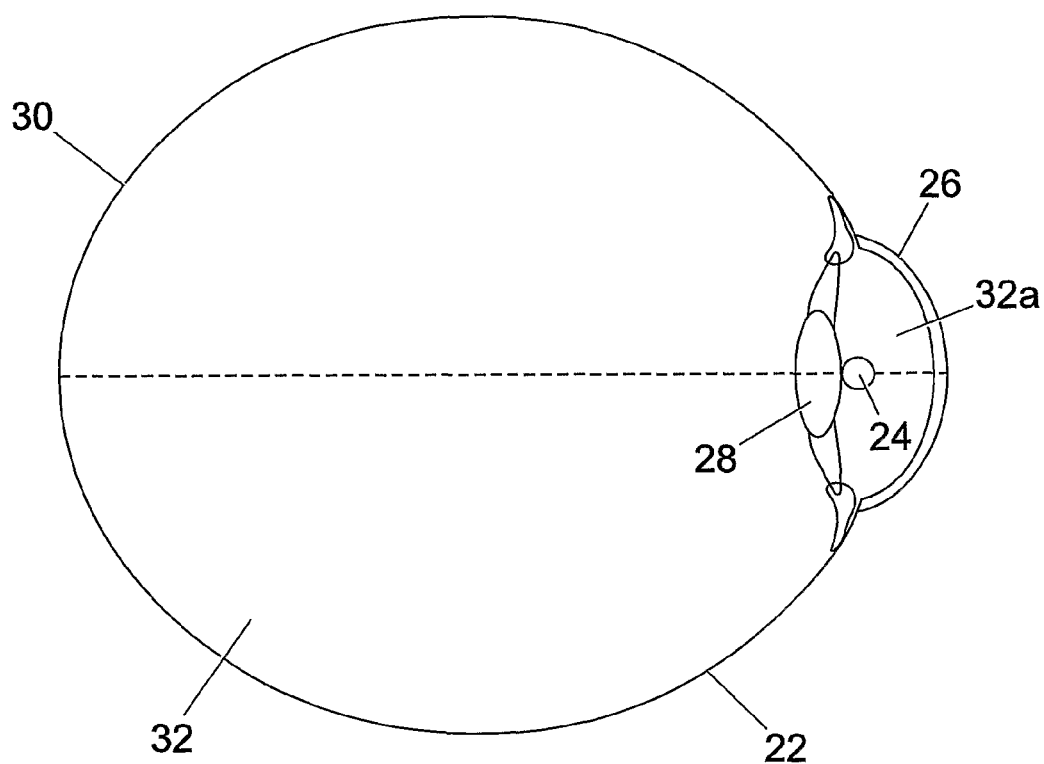
FIG. 2 is a diagram of the subject's eye, detailing the position of an apparent point source of the imaging system of FIG. 1 in relation to the cornea and the lens of the subject's eye.

As described above, the two-dimensional raster scan pattern of the laser beam 13 is transmitted through the pupil of the subject's eye 22. In order to achieve this, the apparent point source of the raster scan pattern is positioned at the first focus of the main mirror 20 and the pupil of the eye is positioned at the second focus of the main mirror 20. This is essentially the same as transferring the apparent point source from the first focus point of the main mirror 20 to the pupillary point of the subject's eye 22. Therefore, the apparent point source may be considered to be located at the pupillary point of the subject's eye 22. As illustrated in FIG. 2, the apparent point source 24 is located between the cornea 26 and the lens 28 of the subject's eye 22.

As the laser beam 13 enters the subject's eye 22 it undergoes refraction by the cornea 26 and the lens 28 of the subject's eye 22. This introduces a distortion into the image obtained from the scanning ophthalmoscope 10. The distortion in this case causes the image to be distorted in both vertical and horizontal directions. The distortion is a combination of refraction of the laser beam 13 by the cornea 26 and the lens 28.

The distortion introduced into the image may be determined by creating a mathematical model of the subject's eye 22, and determining the undistorted path of the laser beam 13 from the main mirror 20 to the retina. The path of the laser beam 13 through the cornea 26 and through the lens 28 is determined over the full two-dimensional raster scan pattern.

The determination of the undistorted path of the laser beam 13 is based on an approximation of the refractive index of the cornea 26, the lens 28, the vitreous humour 32 and the aqueous humour 32a and a knowledge of the laser beam 13 input angles into the subject's eye 22.

The difference between the undistorted path of the laser beam 13 and the distorted or measured path provides the distortion introduced by the cornea 26 and lens 28 of the subject's eye into the image obtained from the scanning ophthalmoscope 10.

Once this distortion is determined, a correction may be applied to the retinal image to substantially remove the effects of this distortion on the retinal image.

The above describes how a two-dimensional wide-field retinal image may be obtained which has been corrected to take into account distortions occurring within the scanning ophthalmoscope 10 and the subject's eye 22. This image may be used as the basis for creating a three-dimensional image of a part of the retina.

Once the two-dimensional wide-field retinal image has been obtained, it is necessary to determine a three-dimensional shape for the imaged part of the retina, i.e. the part of the retina scanned by the laser beam 13.

The shape of the part of the retina scanned by the laser beam 13 may be determined by firstly assigning a shape to the whole of the subject's retina. Typically, the assigned shape is a general shape, which is known to approximate the shape of an eye, such as an ellipsoid. The assigned ellipsoidal shape may then be modified to provide a specific ellipsoidal shape for the whole of the retina of the subject, by measuring the major and/or minor axes of the subject's eye and using the measurements to modify the assigned ellipsoidal shape to obtain the specific ellipsoidal shape for the whole of the subject's retina. The specific ellipsoidal shape for the whole of the subject's retina may thus be represented by a modified mathematical equation of the assigned ellipsoid.

Once the shape of the whole of the subject's retina has been determined, it is necessary to identify the position of the part of the retina scanned by the laser beam 13 with respect to the whole of the subject's retina. This may be achieved by determining the path of the scan of the laser beam 13, and calculating the position of each intersection of the laser beam 13 with the specific ellipsoidal shape for the whole of the subject's retina. The position of each intersection of the laser beam scan and the subject's retina may be calculated by creating a mathematical model of the path of the laser beam 13 within the subject's eye 22. The mathematical model includes the modified mathematical equation of the assigned ellipsoid, i.e. includes the specific ellipsoidal shape for the whole of the subject's retina. The mathematical model of the laser beam 13 within the subject's eye 22 may also include a positional offset component of the subject's eye 22, which represents the difference between the actual position of the subject's eye 22 and an ideal position of the subject's eye with respect to the scanning ophthalmoscope 10. The actual position of the subject's eye 22 may be obtained by using digital image analysis to detect the position of the macula and optic disc. This will take into account, for example, tilt of the subject's head relative to the ophthalmoscope 10.

Figure 3:
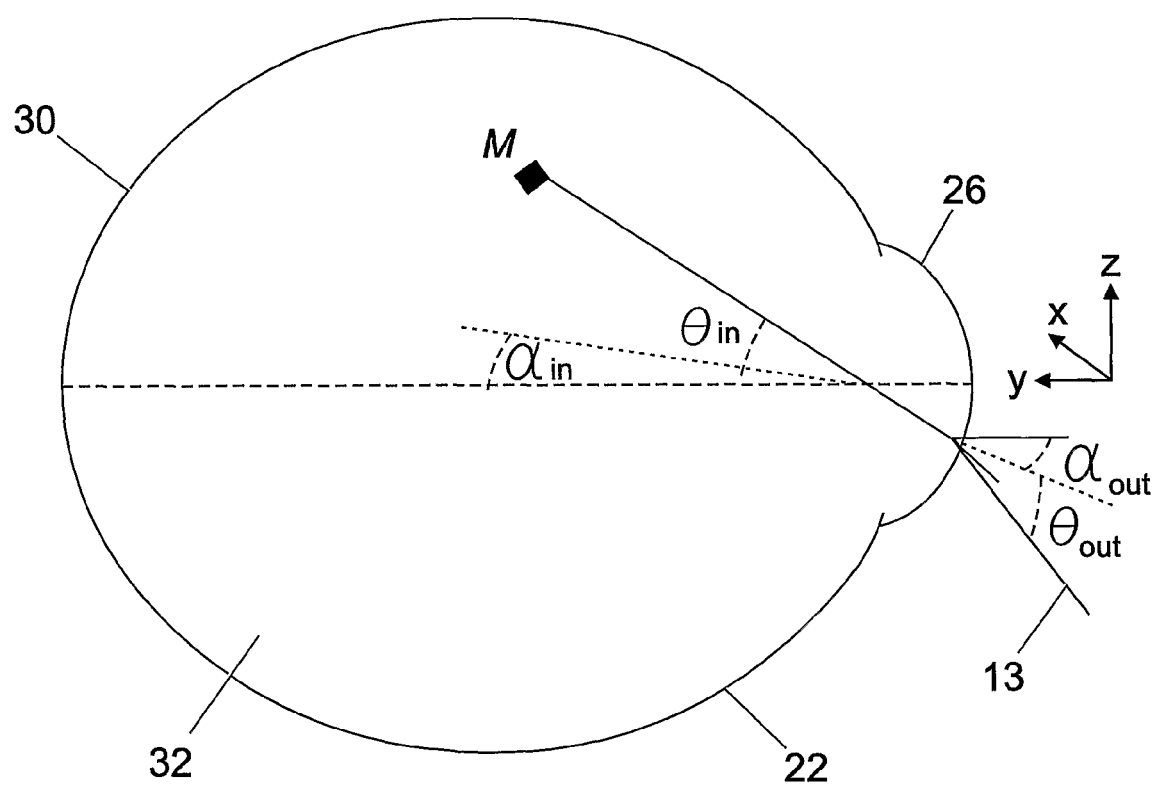
FIG. 3 is a diagram of the subject's eye detailing the path of the collimated light from the imaging system of FIG. 1 to the retina of the eye.

FIG. 3 illustrates the path of the laser beam 13 from the scanning ophthalmoscope (not shown) into the subject's eye and onto the retina 30. It should be noted that only the refraction of the laser beam 13 by the cornea 26 has been illustrated, the refraction of the laser beam 13 by the lens 28 (not shown), the aqueous humour 32 and the vitreous humour 32a have been omitted for clarity.

The laser beam 13 enters the eye through the cornea 26 at angles $\alpha_{out}$ in the direction of the z-axis (vertical), and at angles of $\theta_{out}$ in the direction of the x-axis (horizontal). The laser beam 13 is refracted by the cornea 26 and the lens 28, as described above. The laser beam 13 thus proceeds through vitreous humour 32 of the eye at angles $\alpha_{in}$ in the direction of the z-axis (vertical), and at angles of $\theta_{in}$ in the direction of the x-axis (horizontal). One example of which is illustrated in FIG. 3.

The position of each intersection of the laser beam and the subject's retina 30, labelled M, may then be calculated. The calculation is based on a knowledge of the angles $\alpha_{in}$ and $\theta_{in}$ for the raster scan pattern and the modified mathematical equation of the assigned ellipsoid, i.e. the specific ellipsoidal shape of the whole of the subject's retina 30. The position of each intersection of the laser beam 13 and the subject's retina 30 over the full raster scan is calculated. This determines the position of the part of the retina which is scanned by the laser beam 13 with respect to the whole of the subject's retina 30.

A knowledge of the shape of the whole of the subject's retina 30 and the position of the part of the retina scanned by the laser beam 13 relative to the whole of the subject's retina 30, allows the three-dimensional shape of the part of the retina to be determined.

The above describes a method of obtaining a two-dimensional wide-field image of a part of a retina, and a method of determining a three-dimensional shape for the part of the retina to which the image relates. Once these are known it is possible to produce a three-dimensional image of the part of the retina.

A three-dimensional image of the part of the retina may be produced by using the three-dimensional shape for the part of the retina to modify the two-dimensional wide-field image of the part of the retina. The two-dimensional wide-field image of the part of the retina may be modified by mapping portions of the two-dimensional image to the three-dimensional shape for the part of the retina. That is, for each portion of the two-dimensional image, the position of the portion of the image is mapped to its corresponding position of origin on the three-dimensional shape. The positions of origin on the three-dimensional shape are known as they are defined by angles $\alpha_{in}$ and $\theta_{in}$ of the raster scan pattern, as described above. The three-dimensional image of the part of the retina thus produced, is an accurate representation of the part of the subject's retina 30.

The method of the present invention obviates or mitigates the disadvantages of previous proposals. The three-dimensional image of the part of the retina is based on a two-dimensional wide-field image of the part of the retina. As described above, the two-dimensional image is obtained in a single scanning process and can cover up to 150 degrees of the retina (measured from the pupillary point). Therefore, the three-dimensional image is a "one-piece" image which covers an extremely large area of the retina 30.

Furthermore, the three-dimensional image of the part of the retina facilitates absolute measurement of retinal features. Since the three-dimensional shape of the part of the retina is known, the distance between two retinal points (e.g. $M_1$ and $M_2$) may be easily calculated. This is extremely beneficial for disease diagnosis and monitoring, as the size and growth of, for example, a cancer tumour may accurately be determined.

Also, as the position of the imaged part of the retina is calculated with respect to a subject-specific retinal model, the location of the imaged part of the retina is known relative to the whole of the subject's retina 30. This is extremely beneficial in the treatment of, for example, a cancer tumour, as this ensures that treatment may be applied to the correct part of the retina.

Modifications and improvements may be made to the above without departing from the scope of the present invention.

For example, it should be appreciated that the two-dimensional wide-field retinal image may be a pixelated image, each pixel having a corresponding position of origin on the three-dimensional shape of the imaged part of the retina. With a pixelated image, each pixel may be mapped to its corresponding position on the three-dimensional shape. However, in order to aid processing, it is possible to map a smaller number of "reference" pixels to the three-dimensional shape and interpolate the image data between the "reference" pixels.

Furthermore, a graphical display module may receive a three-dimensional image of the part of the retina and may be used to pan, zoom and rotate the three-dimensional image of the part of the retina. This is especially useful as it allows the user (e.g. an ophthalmologist) to view the image from a number of positions.

Also, although a corrected two-dimensional wide-field image of the part of the retina has been described above as forming the basis of the three-dimensional image, it should be appreciated that an un-corrected two-dimensional wide-field image may be used, e.g. in applications where the distortions introduced by the scanning ophthalmoscope 10 and/or the subject's eye 22 are acceptable.

It should also be appreciated that the two-dimensional image may be partially corrected by correcting for any combination of distortions introduced by the scanning ophthalmoscope 10, slit mirror 18, main mirror 20, or subject's eye 22.

Furthermore, it should be appreciated that the correction for the distortions introduced by the scanning ophthalmoscope 10 and the subject's eye 22 may be applied when modifying the two-dimensional wide-field image with the three-dimensional shape of the imaged part of the retina, i.e. the corrections may be applied when the portions of the two-dimensional wide-field retinal image are mapped to the three-dimensional shape, thus obtaining a corrected three-dimensional image of the retina.

Also, although steps have been described above concerning obtaining a two-dimensional wide-field image of a part of a retina and using this image to produce a three-dimensional image, it should be appreciated that the method is also applicable to any wide-field image of a part of a retina, such as a previously-recorded image of a retina.

Furthermore, although the determination of the path of the laser beam 13 has been described above as being based on an approximation of the refractive index of the cornea 26, the lens 28, the vitreous humour 32 and the aqueous humour 32a and a knowledge of the laser beam 13 input angles, it should be appreciated that the determination may also take into consideration the surface shape of the cornea 26 and the lens 28. This provides a more accurate determination of the distortion. Furthermore, instead of using a fixed approximation of the refractive index of the cornea 26 and lens 28, the determination may use a refractive index which is a function of laser beam input angle.

Also, although the three-dimensional image of the part of the retina has been described above as being obtained by mapping the two-dimensional image of the part of the retina to the three-dimensional shape of the part of the retina, it should be appreciated that only a portion of the image may be mapped to the three-dimensional shape. Furthermore, it should be appreciated that only a portion of the three-dimensional shape of the part of the retina may be determined.

The invention claimed is:

1. A method of producing a three-dimensional image of at least a part of the retina of an eye comprising the steps of:
using an imaging system to obtain a two-dimensional wide-field image of said part of said retina;
using a three-dimensional shape determination module to determine a three-dimensional shape for said part of said retina; and
using a two-dimensional image modification module to modify said two-dimensional wide-field image of said part of said retina using the three-dimensional shape for said part of said retina to produce a three-dimensional image of said part of said retina,
wherein
the step of using a three-dimensional shape determination module to determine a three-dimensional shape for said part of said retina includes the steps of:
assigning a shape to the whole of said retina;
identifying the position of said part of said retina with respect to said whole of said retina; and
using said assigned shape and said position of said part of said retina to determine said three-dimensional shape for said part of said retina, and
wherein the step of assigning a shape to said whole of said retina includes selecting a general shape which approximates the shape of an eye and measuring at least one parameter of said retina, and using said at least one parameter to modify said general shape to obtain a specific shape of said whole of said retina of said eye, and assigning said specific shape to said whole of said retina, and
wherein the step of identifying said position of said part of said retina with respect to said whole of said retina includes:
determining a path of collimated light used to obtain said two-dimensional wide-field image of said put of said retina; and
calculating the position of intersection of said path of said collimated light with said specific shape of said whole of said retina, and
wherein the step of determining said path of said collimated light includes calculating said path of said collimated light from a source of collimated light to said retina, and
wherein said calculation of said path of said collimated light includes determining distortion of said collimated light produced by the cornea of said eye and/or the lens of said eye.

2. A method of producing a three-dimensional image of at least a part of the retina of an eye according to claim 1, wherein the step of using an imaging system to obtain a two-dimensional wide-field image of said part, of said retina includes receiving is previously-recorded image of said part of said retina.

3. A method of producing a three-dimensional image of at least a part of the retina of an eye according to claim 1 wherein the step of using an imaging system to obtain a two-dimensional wide-field image of said part of said retina includes scanning said part of said retina with collimated light.

4. A method of producing a three-dimensional image of at least a part of the retina of an eye according to claim 3 wherein scanning said part of said retina with said collimated light includes:
providing a source of said collimated light, a first scanning element, a second scanning element and a scan compensator;
using said source of said collimated light, said first and second scanning elements and said scan compensator in combination to provide a two-dimensional collimated light scan from an apparent point source;
providing a scan transfer device having two foci;
providing said apparent point source at a first focus of said scan transfer device and accommodating said eye at said second focus of said scan transfer device; and
using said scan transfer device to transfer said two-dimensional collimated light scan from said apparent point source to said eye to obtain a two-dimensional wide-field image of said part of said retina.

5. A method of producing a three-dimensional image of at least a part of the retina of an eye according claim 1 wherein said two-dimensional wide-field image of said part of said retina is modified by mapping a portion of said image to said three-dimensional shape for said part of said retina to produce said three-dimensional image of said part of said retina.

6. A method of producing a three-dimensional image of it least a part of the retina of an eye according to claim 1, wherein said general shape is an ellipsoid and said parameter includes the major axis or minor axis of said whole of said retina.

7. A method of producing a three-dimensional image of at least a part of the retina of an eye according to claim 1, wherein the stop of calculating the position of intersection of said path of said collimated light with said specific shape of said whole of said retina, includes the further step of determining the position of said whole of said retina relative to an ideal position of said whole of said retina.

8. A method of producing a three-dimensional image of at least a part of the retina of an eye according to claim 1 wherein said calculation of said path of said collimated light includes determining distortion of said collimated light produced by said scan compensator.

9. A method of producing a three-dimensional image of it least a part of the retina of an eye according to claim 1, wherein said calculation of said path of said collimated light includes determining distortion of said collimated light produced by said scan transfer device.

10. A method of producing a three-dimensional image of it least a part of the retina of an eye according to claim 1, wherein said two-dimensional wide-field image of said part of said retina comprises a plurality of pixels.

11. A method of producing a three-dimensional image of at least a part of the retina of an eye according to claim 10, wherein said two-dimensional wide-field image of said part of said retina is modified by mapping said plurality of pixels to said three-dimensional shape for said part of said retina to produce said three-dimensional image of said part of said retina.

12. A method of producing a three-dimensional image of at least a part of the retina of an eye according to claim 11, wherein said mapping of said plurality of pixels includes interpolating image data contained in one or more of said pixels.

13. An apparatus for producing a three-dimensional image of at least a part of the retina of an eye comprising:
an imaging system adapted to provide a two-dimensional wide-field image of said part of said retina;
a three-dimensional shape determination module adapted to determine a three-dimensional shape for said part of said retina; and a two-dimensional image modification module adapted to modify said two-dimensional wide-field image of said part of said retina using said three-dimensional shale to produce a three-dimensional image of said part of said retina, wherein the three-dimensional shape determination module is adapted to:

assign a shape to the whole of said retina;

identify the position of said part of said retina to said whole of said retina; and use said assigned shape and said position of said part of said retina to determine said three-dimensional shape for said part of said retina, and wherein the assignment of a shape to said whole of said retina includes selecting a general shape which approximates the shape of an eye and measuring at least one parameter of said retina, and using said at least one parameter to modify said general shape to obtain a specific shape of said whole of said retina of said eye, and assigning said specific shape to said whole of said retina, and wherein identification of said position of said part of said retina with respect to said whole of said retina includes:

determining a path of collimated light used to obtain said two-dimensional wide-field image of said part of said retina; and calculating the position of intersection of said path of said collimated light with said specific shape of said whole of said retina, and wherein determination of said path of said collimated light includes calculating said path of said collimated light from said source of collimated light to said retina, and wherein said calculation of said path of said collimated light includes determining distortion of said collimated light produced by the cornea of said eye and/or the lens of said eye.

14. An apparatus for producing a three-dimensional image of at least a part of the retina of an eye as claimed in claim 13, wherein said imaging system comprises:

a source of collimated light;

a first scanning element;

a second scanning element; and a scan compensator;

wherein said source of collimated light, said first and second scanning elements and said scan compensator combine to provide a two-dimensional collimated light scan from an apparent point source;

said apparatus further comprising a scan transfer device, wherein said scan transfer device has two foci and said apparent point source is provided at a first focus of said scan transfer device and an eye is accommodated at it second focus of said scan transfer device, and wherein said scan transfer device transfers said two-dimensional collimated light scan from said apparent point source into said eye to obtain a two-dimensional image of said part of said retina.

* * * * *

UNITED STATES PATENT AND TRADEMARK OFFICE
CERTIFICATE OF CORRECTION

PATENT NO. : 8,422,750 B2  
APPLICATION NO. : 12/312421  
DATED : April 16, 2013  
INVENTOR(S) : Alastair Atkinson et al.

Page 1 of 1

It is certified that error appears in the above-identified patent and that said Letters Patent is hereby corrected as shown below:

On the title page item (73), correct Assignee from "Optos, PLC" to "Optos Plc"

In the Claims:

Column 9, line 40, "put" should read "part"

Column 10, line 40, "it" should read "at"

Column 10, line 45, "it" should read "at"

Column 11, line 3, "shale" should read "shape"

Column 12, line 23, "it" should read "a"

Signed and Sealed this  
Seventeenth Day of September, 2013

Teresa Stanek Rea  
*Deputy Director of the United States Patent and Trademark Office*